United States Patent [19]

Schmidt et al.

[11] Patent Number: 4,749,495

[45] Date of Patent: Jun. 7, 1988

[54] PROCESS FOR SEPARATING OXYGENOUS ORGANIC COMPOUNDS FROM AQUEOUS MEDIA

[75] Inventors: Alfred Schmidt; Alfred Windsperger; Anton Friedl, all of Vienna, Austria

[73] Assignee: Vogelbusch Gesellschaft m.b.H., Austria

[21] Appl. No.: 7,662

[22] Filed: Jan. 28, 1987

[30] Foreign Application Priority Data

Feb. 6, 1986 [AT] Austria .................................. 289/86

[51] Int. Cl.$^4$ .......................... C02F 1/26; C07C 31/02
[52] U.S. Cl. .................................... 210/634; 210/908; 210/927
[58] Field of Search .............. 210/634, 644, 645, 908, 210/927

[56] References Cited

FOREIGN PATENT DOCUMENTS 3112603 11/1982 Fed. Rep. of Germany .

*Primary Examiner*—Tom Wyse
*Attorney, Agent, or Firm*—Ostrolenk, Faber, Gerb & Soffen

[57] ABSTRACT

A process for separating oxygenous organic compounds from aqueous media by liquid-liquid extraction with an organic extraction agent. In order to enable the satisfactory and selective separation of the organic compounds without remarkable amounts of extraction agent remaining dissolved in the raffinate and without microorganisms possibly present in the aqueous media being impaired, an extraction agent is used that contains up to 100% by mass of at least one aldehyde including 4 to 20 carbon atoms.

8 Claims, No Drawings

PROCESS FOR SEPARATING OXYGENOUS ORGANIC COMPOUNDS FROM AQUEOUS MEDIA

FIELD OF THE INVENTION

The invention relates to a process for the separation of oxygenous organic compounds, such as alcohols, aldehydes, ketones, ethers, higher carboxylic acids and esters, from aqueous media by liquid-liquid extraction with an organic extraction agent.

Examples of oxygenous organic compounds that may be separated from aqueous media according to the invention are ethanol, amyl alcohols, butanol, acetone and furfural.

BACKGROUND OF THE INVENTION

When oxygenous compounds are separated by distillation, a high energy consumption must be taken into account. In addition, for instance, with the recovery of fermentation products from fermentation mashes, the temperature load during distillation must be considered, which cannot be totally avoided even by cumbersome vacuum distillation. The heating of mashes to elevated temperatures, however, prevents the mashes, which have largely been freed from fermentation products, from being recycled into the fermentation stage.

Yet, it is the separation of the initially mentioned compounds which is of a major importance to the recovery of the products of fermentation processes from aqueous fermentation media:

So far, relatively dilute mashes, as a rule, have been used for fermentation, for instance, with the large-scale production of ethanol by alcoholic fermentation, because the fermentation product ethanol has a toxic effect on the microorganisms used for fermentation already from concentrations of about 5%, which inhibits fermentation. The fermentation process mostly is carried out discontinuously, processing of the fermented mash being effected by distillation. As a result of the high mash dilutions required, large amounts of water must be conducted through the individual process stages with a correspondingly high consumption of energy involved.

By advances in raw material processing and distillation, the energy demand will be lowered only slightly.

Therefore, there has been the endeavor to attain a further increase in productivity and a further decrease of energy demand by employing concentrated mashes and fermentation media as well as by carrying out fermentation continuously. Yet, concentrated mashes can be fermented only if the concentration of the fermentation products—such as ethanol—is maintained below the inhibiting threshold during fermentation.

Basically, the direct removal from the fermentor, such as, e.g., by vacuum fermentation or by $CO_2$ stripping, or the separation by circulation of the mash through an external separating system are feasible to separate the product from the fermentation mash during fermentation.

The realization of vacuum fermentation raises problems with regard to fermentation control, in particular with technical plants, moreover, the subsequent compression of the carbonic acid formed is uneconomical.

The separation of the fermentation product by stripping with $CO_2$, so far, has been tested primarily on a laboratory scale; with the separation performances required, disturbances of fermentation may occur.

As external separation systems, adsorption, extraction, membrane methods or methods employing liquid-steam enrichment may be used.

As extraction agents for liquid-liquid extraction, most of the current solvents have already been tested. Yet, the solvents in question have relatively high solubilities in water or in the aqueous fermentation medium and mostly have strongly toxic effects on the microorganisms used for the fermentation.

The same considerations with respect to substrate concentration in fermentation liquors and to economical fermentation control hold for other types of fermentation, for instance, butanol-acetone fermentation.

In DE-A No. 31 12 603, a three-stage process for the separation of lower aliphatic alcohols from fermentation liquors is described. The only recoverable fermentation product expressly mentioned is ethanol.

In the first stage, the fermentation liquor preferably is extracted with a higher n-alcohol. To recover the residual content of the solvent used in the first extraction stage from the aqueous raffinate phase obtained, the raffinate phase, in the second stage, is extracted with an a polar second solvent, in particular with an alkane having 5 to 18 carbon atoms. The two solvents consecutively used for the extraction again must be separated from each other in a third stage.

To realize the known process, two extraction devices and two separating devices are necessary. Thus, this process requires extensive energy and apparatus means. Add to this that the extraction is to take place at system temperatures as high as possible, up to 60° C.

SUMMARY OF THE INVENTION

It is an object of the invention to eliminate the difficulties and disadvantages of known separation processes pointed out above and to enable the satisfactory and selective separation of oxygenous organic compounds from aqueous media without remarkable amounts of extraction agent remaining dissolved in the aqueous raffinate and without microorganism cultures possibly present in the aqueous media being impaired by toxic effects.

According to the invention, this object is achieved by extraction with an agent comprising up to 100% by mass of at least one aldehyde having 4 to 20 carbon atoms.

An oxygenous organic compound may be separated from aqueous media provided it does not enter into chemical reactions with the aldehydes used in each case.

The application of the process according to this invention offers advantages in two aspects:

In terms of product separation from product-containing solutions, an energy-saving product separation with few apparatus is feasible because of the favorable equilibrium conditions prevailing.

Product separation in an external recirculating system enables the processing of concentrated substrates or mashes, with the overall energy consumption being drastically reduced on account of the much lower amount of entrained ballast water involved. In this manner, fermentation products can be separated at time intervals or continuously. For continuous separation, a partial stream of the aqueous medium may be drawn from fermentation and treated with the extraction agent, for instance, in one or several liquid-liquid extraction columns. Any type of known extraction columns, such as columns with stirring organs, may be used. The aqueous raffinate can be returned to fermentation at least partially.

As compared to the extraction agents mentioned further above—higher monovalent alcohols, for instance—, the aldehydes are far less soluble in aqueous media. Thus, losses of the extraction agents used according to the invention may be kept very low even without the subsequent extraction of the same from the aqueous raffinate. They are also less toxic to microorganisms which may be present. Because they are present in the raffinate in extremely low concentrations only, they have practically no fermentation inhibiting effect.

Even the distribution coefficients of the compounds to be separated between aldehyde-containing extraction agents and aqueous media are higher than those of solvents used for extraction so far.

DETAILED DESCRIPTION OF CERTAIN PREFERRED EMBODIMENTS

Probably, an extraction agent with an aldehyde content of at least 10% is used.

The remaining portion of the extraction agent may be comprised of other more or less polar solvents which have low solubility in water, such as higher alkanes and alcohols, ketones, e.g., diisobutyl ketone, quinoline or pyridine derivatives.

Preferably, the extraction agent contains at least one aliphatic aldehyde including a straight or branched carbon chain.

Particularly preferred extraction agents are pentanal, hexanal, heptanal or a mixture of at least two of these aldehydes.

The solubility of hexanal in pure water is 0.1% by mass; heptanal is soluble in pure water even by less than 0.01% by mass (based on 20° C).

The solubility of the corresponding alcohols in pure water is significantly higher, amounting to 0.5% by mass with hexanol and 0.17% by mass with heptanol.

Diisobutyl ketone, which is frequently used for extraction purposes, is soluble in aqueous media by about 0.1% by mass.

According to one embodiment of the invention, hexanal or heptanal is used as extraction agent to separate ethanol from aqueous fermentation media.

According to another embodiment, heptanal is employed as extraction agent for the simultaneous separation of butanol and acetone from aqueous fermentation media.

The determination of the equilibrium parameters was effected in a double shell glass jar thermostatized to 20° C. and including a discharge means to separate the aqueous phase from the organic one. Because of the double shell glass jar, it was possible to observe mixing and separating of the phases such that even the rate of deposition of the solvent phase from the aqueous phase could be estimated. The intimate mixing necessary for the mass transfer was effected by means of a motor-driven stirrer, whose shaft had been introduced into the vessel in a gas-tight manner. Thus, the evaporation of the compound to be separated, of water, and of extraction agent was prevented. The thoroughly separated phases were filled into test tubes, the latter were tightly closed by rubber plugs. Not later than on the subsequent day, the phases were analyzed by gas chromatography.

From the analysis data, the distribution coefficient, the selectivity and the solubility of the extraction agent in water were evaluated.

The invention will now be explained in more detail by way of the following examples.

EXAMPLE 1

Separation of ethanol (a) An aqueous solution having an ethanol content of 7% by mass is treated with an equal amount of hexanal in the above-described jar. An extraction solution having an ethanol content of 3.6% by mass is obtained. The ethanol concentration in the aqueous raffinate decreases to 3.3% by mass. The concentration of hexanal in the raffinate was not more than 0.2% by mass.

(b) Under the same conditions as described in a), heptanal was employed as extraction agent. The ethanol concentrations were:
3.2% by mass in the extract
3.8% by mass in the raffinate.

The heptanal content in the aqueous raffinate was practically negligible, which is of the greatest importance to the extremely sensitive microorganisms present in the aqueous medium.

The distribution coefficients with 10% ethanol in the extract phase are 1.29 for hexanal as extraction agent and 1.31 for pentanal as extraction agent.

The distribution coefficient for the distribution of ethanol between heptanal and water, which had been determined accordingly, amounted to 0.94.

The extraction of ethanol, which is difficult on account of the slight differences in polarity of ethanol and water, according to the process of this invention is feasible in an economical and operationally safe manner. The distribution coefficients to a major extent are above 1; thus, an effective decrease of the product concentration will be obtained by few separation stages (i.e., by extraction columns of low structural heights).

COMPARATIVE EXAMPLE 1

(a) When using n-hexanol as extraction agent, an ethanol concentration of only 3.3% by mass in the extract and a higher concentration of 3.7% by mass in the raffinate will result. The solubility of hexanol in aqueous media is larger so that its concentration in the raffinate is 0.6% by mass.

(b) If n-heptanol is used as extraction agent, the concentration of ethanol in the extract is even lower, i.e., about 3.0% by mass. The respective raffinate concentration will be 4.0% by mass of ethanol.

EXAMPLE 2

Separation of butanol and acetone (a) Since, e.g., with acetone-butanol fermentation, the inhibition of the production of microorganisms starts already below 2% by mass of butanol in the mash (in the fermentation medium), it was departed from 1.8% by mass aqueous butanol solutions in the extraction assays. One-stage extraction with equal amounts of heptanal yielded 1.6% by mass of butanol in the organic extraction phase and a reduction of the butanol concentration in the aqueous raffinate to 0.13% by mass. The solubility of heptanal in the raffinate is low, lying below 0.01% as in pure water.

The distribution coefficient for 1.7% butanol in the extract phase amounts to 12.9.

(b) When employing the process according to the invention to acetone-butanol fermentation, the simultaneous separation of the by-product acetone is essential. With heptanal as extraction agent, the concentrations, based on an aqueous medium with 2.1% by mass of acetone, amount to 0.95% by mass in the extract and 1.15% by mass in the raffinate, thus being significantly better than with conventional solvents, if the extraction is again carried out in one stage as described under (a).

The distribution coefficient is 0.83 (acetone between heptanal and water).

COMPARATIVE EXAMPLE 2

(a) If one departs from a solution containing 1.8% by mass of butanol in water as in example 2(a) and extracts with an equal amount of heptanol in one stage, there will be 1.65% by mass of butanol in the extract and 0.15% by mass of butanol in the raffinate. The raffinate, however, also contains at least 0.1% by mass of extraction agent.

(b) Analogous to Example 2(b), the following concentrations of acetone were determined with heptanol being used as extraction agent:

0.8% by mass in the extract
1.2% by mass in the raffinate.

It is apparent that heptanal is more apt as an extraction agent than usual solvents, for commonly separating the products butanol, acetone and ethanol incurring simultaneously in an aqueous medium, e.g., at the butanol-acetone fermentation.

What we claim is:

1. A process for extracting oxygenous organic compounds from aqueous media comprising the steps of contacting said media with an organic extraction agent having up to 100% by mass of at least one aldehyde comprising 4 to 20 carbon atoms, and thereafter separating said media from said organic extraction agent.

2. The process according to claim 1, wherein said aldehyde is present at a contraction of at least 10% by mass.

3. The process according to claim 1, wherein said organic extraction agent comprises at least one aliphatic aldehyde including a straight carbon chain.

4. The process according to claim 1, wherein said organic extraction agent comprises at least one aliphatic aldehyde including a branched carbon chain.

5. The process according to claim 1, wherein said organic extraction agent comprises an aldehyde selected from the group consisting of pentanal, hexanal, heptanal and a mixture of at least two of these aldehydes.

6. The process according to claim 1, wherein ethanol is separated from aqueous fermentation media and said extraction agent is comprised of hexanal.

7. The process according to claim 1, wherein ethanol is separated from aqueous fermentation media and said extraction agent is comprised of heptanal.

8. The process according to claim 1, wherein butanol and acetone are simultaneously separated from aqueous fermentation media and said extraction agent is comprised of heptanal.

* * * * *

UNITED STATES PATENT AND TRADEMARK OFFICE
CERTIFICATE OF CORRECTION

PATENT NO. : 4,749,495

DATED : June 7, 1988

INVENTOR(S) : Alfred SCHMIDT ET AL.

It is certified that error appears in the above-identified patent and that said Letters Patent is hereby corrected as shown below:

In claim 2, line 2, "contraction" should read --concentration--.

Signed and Sealed this

Twenty-fourth Day of January, 1989

Attest:

DONALD J. QUIGG

Attesting Officer    Commissioner of Patents and Trademarks